(12) United States Patent
Yeh

(10) Patent No.: US 8,177,359 B2
(45) Date of Patent: May 15, 2012

(54) HEALTH-CARING GLASSES

(75) Inventor: Kuo-Jen Yeh, Tainan (TW)

(73) Assignee: Jung Hou, Jr., Yongkang, Tainan (TW)

( * ) Notice: Subject to any disclaimer, the term of this patent is extended or adjusted under 35 U.S.C. 154(b) by 145 days.

(21) Appl. No.: 12/856,680

(22) Filed: Aug. 15, 2010

(65) Prior Publication Data
US 2011/0234971 A1     Sep. 29, 2011

(30) Foreign Application Priority Data
Mar. 23, 2010   (TW) ............................... 99205019 U

(51) Int. Cl.
*G02C 5/14*    (2006.01)
*A61H 1/00*    (2006.01)

(52) U.S. Cl. ........................... 351/111; 351/136; 601/37

(58) Field of Classification Search ................ 351/41, 351/111, 122, 136, 139; 601/37
See application file for complete search history.

(56) References Cited

U.S. PATENT DOCUMENTS
2002/0080326 A1 *    6/2002   Schleger et al. ............. 351/121
* cited by examiner

*Primary Examiner* — Huy K Mai

(57) ABSTRACT

A pair of health-caring glasses consists of two lenses, a bridge and two temples. The bridge is fixed between the lenses by screws, provided with two nose pads respectively inlaid with a loadstone. The temples are respectively positioned at an outer portion of the lenses, provided with a rubber sleeve made of far infrared material, and a plurality of massage projections closely spread on the rubber sleeve. By means of resonance created by the loadstone, far infrared released by the rubber sleeves and massage projections to massage acupuncture points about head, a user wearing the glasses can ease eyes fatigue, has his or her face beautified and brain stimulated.

1 Claim, 3 Drawing Sheets

HEALTH-CARING GLASSES

BACKGROUND OF THE INVENTION

1. Field of the Invention

This invention relates to a pair of health-caring glasses, particularly to one able to preserve and protect eyes and promote blood circulation of a head.

2. Description of the Prior Art

Commonly, a pair of conventional glasses consists of a frame, two temples and two lenses. With the frame engaged with different functional lenses, the conventional glasses can be employed to correct eyesight, shield off sunlight, and perform as an ornament. But no other health-caring functions are covered. In order to protect eyes or to promote blood circulation of a head, people usually count on particular devices or manual massage, wasting not only time but also money.

SUMMARY OF THE INVENTION

The object of this invention is to offer a pair of glasses that can preserve and protect eyes, and promote blood circulation of a head.

The main characteristics of the invention are two lenses, a bridge and two temples. The bridge is positioned between the lenses. The temples are respectively connected with an outer portion of the lenses. The bridge is provided with two nose pads respectively inlaid with a loadstone. Each of the temples is covered with a rubber sleeve made of far infrared material. Plural massage projections are closely spread on the rubber sleeve.

BRIEF DESCRIPTION OF DRAWINGS

This invention is better understood by referring to the accompanying drawings, wherein.

DETAILED DESCRIPTION OF THE PREFERRED EMBODIMENT

Figure 1:
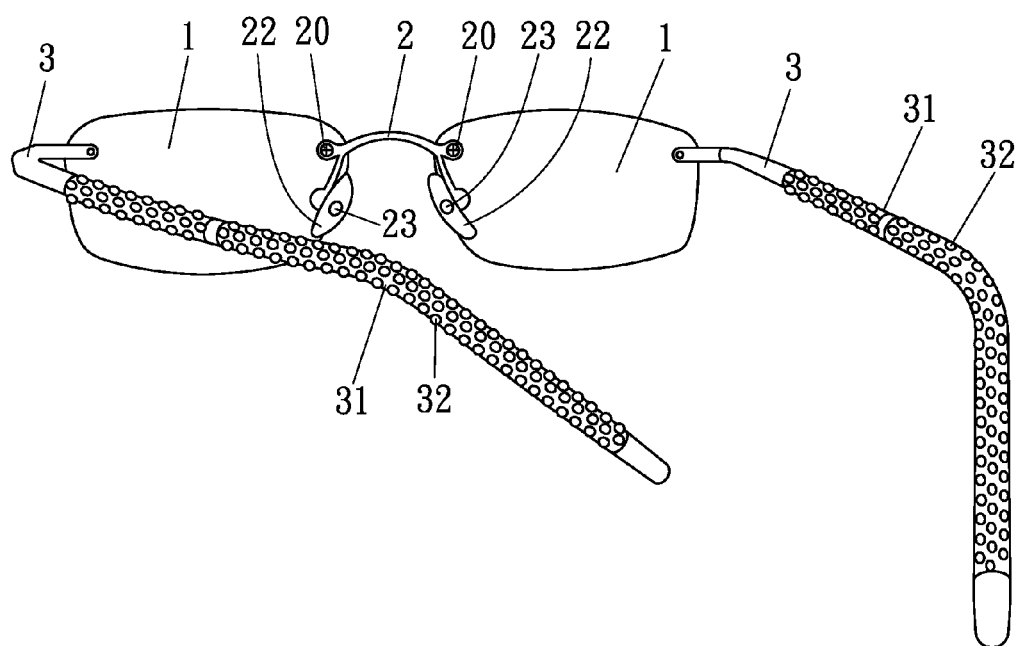
FIG. 1 is a perspective view of a preferred embodiment of a pair of health-caring glasses in the present invention.
Figure 2:
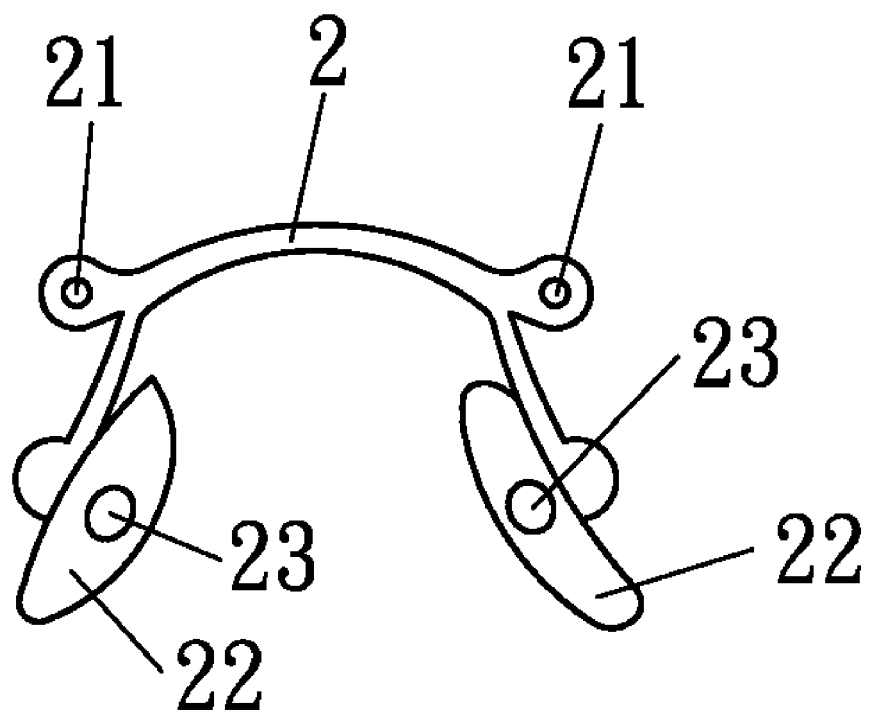
FIG. 2 is a perspective view of a bridge in the preferred embodiment of a pair of health-caring glasses in the present invention.
Figure 3:
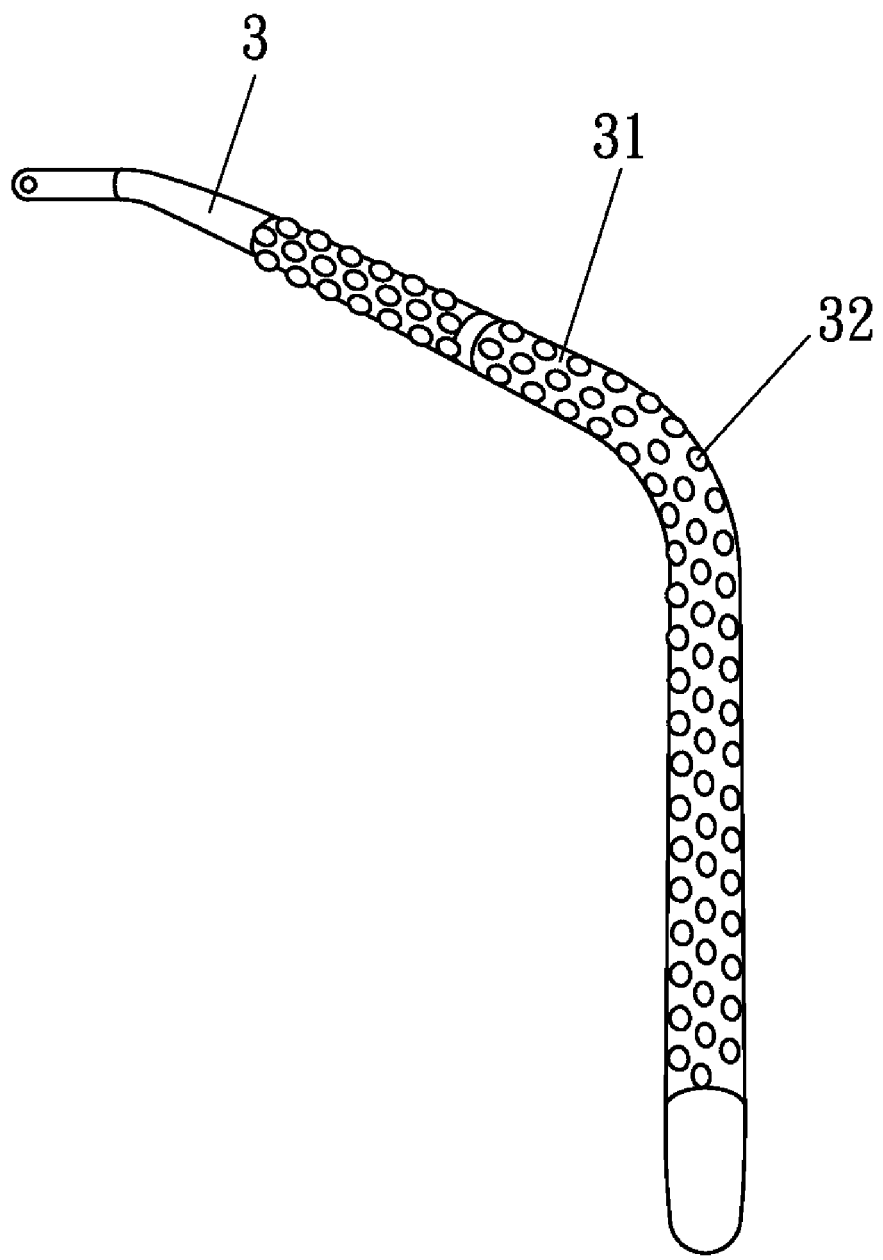
FIG. 3 is a perspective view of a temple in the preferred embodiment of a pair of health-caring glasses in the present invention.

As shown in FIGS. 1~3, a preferred embodiment of a pair of health-caring glasses in the present invention is composed of two lenses 1, a bridge 2 and two temples 3.

The bridge 2 is fixed on between the lenses 1 by screws 20, provided with a through hole 21 bored in two sides respectively, two nose pads 22 and a loadstone 23 inlaid in the center of each of the nose pads 22.

The temples 3 are respectively positioned at the outer portion of the lenses 1, provided with a rubber sleeve 31 made of far infrared material, and a plurality of massage projections 32 closely spread on the rubber sleeve 31.

In using, as shown in FIG. 1, the nose bridge 2 is put on a user's nose, with the loadstones 23 of the nose pads 22 contacting with the skin. Based on resonance of magnetic field, the loadstone 23 will release electric charges and free radicals when temperature rises to as high as 32° C., able to resist oxidization, enhance cells activity and blood circulation of a head, and soothe tired eyes.

Moreover, associated with the loadstones 23, the rubber sleeves 31 of the temples 3 can release far infrared to create a bio-protective magnetic field around a user's head. By means of the massage projections 32, the acupuncture points about eyes and head can be massaged to soothe tiredness, stimulate brain, promote blood circulation and improve health. That is, combining the loadstones 23 and far infrared of the rubber sleeves 31 to stimulate Yuyao point, Chengqi point, Tongziliao point, Jingming point and Taiyang point around eyes can make ciliary muscles relaxed, adjust optic nerves, enhance head blood circulation, soothe eyes tiredness and turgidity and headache, stimulate brain and ease fatigue of eyes, generally achieving health-caring purpose.

While the preferred embodiment of the invention has been described above, it will be recognized and understood that various modifications may be made therein and the appended claims are intended to cover all such modifications that may fall within the spirit and scope of the invention.

What is claimed is:

1. A pair of health-caring glasses comprising two lenses, a bridge positioned between said lenses, two temples respectively connected with an outer portion of said lenses, said bridge provided with two nose pads respectively inlaid with a loadstone, each of said temples covered with a rubber sleeve made of far infrared material, with plural massage projections closely spread on said rubber sleeve.

* * * * *